United States Patent
Ohno et al.

(10) Patent No.: US 7,468,466 B2
(45) Date of Patent: Dec. 23, 2008

(54) PROCESS FOR PRODUCING HEXAFLUOROETHANE AND USE THEREOF

(75) Inventors: Hiromoto Ohno, Kawasaki (JP); Tatsuharu Arai, Kawasaki (JP)

(73) Assignee: Show A Denko K.K., Tokyo (JP)

( * ) Notice: Subject to any disclaimer, the term of this patent is extended or adjusted under 35 U.S.C. 154(b) by 351 days.

(21) Appl. No.: 10/567,757

(22) PCT Filed: Aug. 9, 2004

(86) PCT No.: PCT/JP2004/011709

§ 371 (c)(1),
(2), (4) Date: Feb. 10, 2006

(87) PCT Pub. No.: WO2005/019141

PCT Pub. Date: Mar. 3, 2005

(65) Prior Publication Data

US 2006/0252970 A1    Nov. 9, 2006

Related U.S. Application Data

(60) Provisional application No. 60/498,284, filed on Aug. 28, 2003.

(30) Foreign Application Priority Data

Aug. 21, 2003 (JP) .............................. 2003-208236
Apr. 16, 2004 (JP) .............................. 2004-121604

(51) Int. Cl.
*C07C 17/00* (2006.01)
*C07C 17/28* (2006.01)

(52) U.S. Cl. .................. 570/165; 570/177; 570/178

(58) Field of Classification Search ................. 570/165, 570/177, 178
See application file for complete search history.

(56) References Cited

U.S. PATENT DOCUMENTS

2002/0183568 A1    12/2002   Ohno et al.
2003/0157800 A1     8/2003   Ohno et al.

FOREIGN PATENT DOCUMENTS

| WO | WO 01/98240 A2 | 12/2001 |
| WO | WO 02/18305 A2 | 3/2002 |
| WO | WO 03/014047 A1 | 2/2003 |

*Primary Examiner*—Jafar Parsa
(74) *Attorney, Agent, or Firm*—Sughrue Mion, PLLC

(57) ABSTRACT

A process for producing hexafluoroethane, comprising a step of distilling a crude hexafluoroethane containing chlorine compounds each having two carbon atoms to distill out hexafluoroethane as a top flow from the top of a distillation column and separate a hexafluoroethane mixture containing the chlorine compounds as a bottom flow from the bottom, and a step of contacting the bottom flow with hydrogen fluoride in the gas phase at a temperature of 300 to 500° C. in the presence of a fluorination catalyst to fluorinate the chlorine compounds. This process provides hexafluoroethane which can be used mainly as a cleaning gas in the production process of a semiconductor device.

19 Claims, 1 Drawing Sheet

PROCESS FOR PRODUCING HEXAFLUOROETHANE AND USE THEREOF

CROSS-REFERENCE TO RELATED APPLICATION

This application is an application filed under 35 U.S.C. § 111(a) claiming benefit pursuant to 35 U.S.C. § 119(e)(1) of the filing date of the Provisional Application 60/498,284 filed Aug. 28, 2003, pursuant to 35 U.S.C. § 111(b).

TECHNICAL FIELD

The present invention relates to a process for producing hexafluoroethane and uses thereof.

BACKGROUND ART

Hexafluoroethane ($CF_3CF_3$) is used, for example, as a cleaning or etching gas for semiconductors. With respect to the production process of $CF_3CF_3$, various methods have been heretofore known. Examples thereof include:

(1) a method of fluorinating dichlorotetrafluoroethane, chloropentafluoroethane or the like by using hydrogen fluoride in the presence of a fluorination catalyst, and (2) a method of directly fluorinating tetrafluoroethane and/or pentafluoroethane by using a fluorine gas.

However, for example, when the method of (1) above is used, compounds originated in starting materials or compounds newly produced by the reaction are contained as impurities in the produced $CF_3CF_3$. Among these impurities, chlorine-containing compounds are difficult to separate from $CF_3CF_3$ and become a problem.

Also, when the method of (2) above is used, compounds originated in the starting materials or compounds newly produced by the reaction are contained as impurities in the produced $CF_3CF_3$.

Also, in these impurities, chlorine-containing compounds which are difficult to separate from $CF_3CF_3$ become a problem. To solve this problem, the reaction with a fluorine gas may be performed after purifying the starting material to reduce the chlorine-containing compounds contained therein, but industrial practice of conventionally known purification methods is difficult, in many cases.

Examples of the chlorine-containing compounds contained in $CF_3CF_3$ produced by the above-described method include compounds such as chlorodifluoromethane, chlorotrifluoromethane, dichlorotetrafluoroethane, chloropentafluoroethane, 1-chloro-2,2,2-trifluoroethane, 1,1-dichloro-2,2,2-trifluoroethane and 1-chloro-1,2,2,2-tetrafluoroethane.

Among these chlorine-containing compounds, chlorotrifluoromethane forms an azeotropic mixture with $CF_3CF_3$ and separation of this compound is difficult. As for the method of purifying this chlorotrifluoromethane-containing $CF_3CF_3$, for example, U.S. Pat. No. 5,523,499 describes a process of contacting $CF_3CF_3$ containing trifluoromethane ($CHF_3$) or chlorotrifluoromethane ($CClF_3$) as impurities with an adsorbent such as activated carbon or molecular sieve to adsorb and thereby remove the impurities.

According to the purification method using such an adsorbent, in the case of a stationary operation, the adsorbent must be regenerated approximately at regular intervals and equipment therefor is necessary, though this may vary depending on the impurity content. Also, a large amount of gas may be continuously treated by using, for example, a method of disposing two adsorption tower units and alternately changing over the operation between the step of adsorbing impurities and the step of regenerating the adsorbent, but the chlorotrifluoromethane adsorbed and thereby removed cannot be released as it is into air and must be treated by some method because this is one of specified the fluorocarbons which are thought to deplete the ozone layer.

Furthermore, for example, chloropentafluoroethane ($CF_3CClF_2$) which is one of starting materials for the production of $CF_3CF_3$ does not form an azeotropic mixture with $CF_3CF_3$ but, when remaining in the product, this compound is difficult to separate. For purifying this chloropentafluoroethane, for example, Japanese International Application Domestic Publication No. 9-508626 describes a purification method, using extractive distillation, of adding an extractant. In this purification method using extractive distillation, the extractant added must be recovered through distillation by further using a distillation column, which causes a problem such as increase in the equipment or energy cost, and complete removal of the impurity chloropentafluoroethane can hardly be attained.

Accordingly, chlorine-containing compounds are contained as impurities in the step of producing $CF_3CF_3$ and in the gas produced. The objective $CF_3CF_3$ is usually recovered as a low boiling component from the top of a distillation column and further passed though a purification step to obtain high-purity $CF_3CF_3$ as a product. On the other hand, the chlorine-containing compounds contained as impurities are separated as a high boiling component, that is, as a bottom component of the distillation column. In this bottom component, $CF_3CF_3$ is sometimes contained in a concentration of about 90 to 97 mol %. For example, in the method of producing $CF_3CF_3$ by a reaction of pentafluoroethane with a fluorine gas, the chlorine compounds contained in raw materials do not participate in a displacement reaction with the fluorine gas and therefore, are gradually concentrated in the bottom of the distillation column. According to the degree of concentration, for example, a step of discarding the chlorine-containing compounds by a burning treatment or the like is necessary. However, as described above, high-concentration $CF_3CF_3$ is contained in this bottom component and it is required to recover the $CF_3CF_3$ by a purification operation.

DISCLOSURE OF INVENTION

The present invention has been made under these circumstances and an object of the present invention is to provide a process for industrially advantageously producing hexafluoroethane which can be used mainly as a cleaning gas in the production process of a semiconductor device, and uses of the hexafluoroethane.

As a result of intensive investigations to attain the above-described object, the present inventors have found that hexafluoroethane can be produced with good efficiency by using a process for producing hexafluoroethane, comprising a step of distilling a crude hexafluoroethane containing chlorine compounds each having two carbon atoms to distill out hexafluoroethane as a top flow from the top of a distillation column and separate a hexafluoroethane mixture containing the chlorine compounds as a bottom flow from the bottom of the distillation column, and a step of contacting the bottom flow with hydrogen fluoride in a gas phase at a temperature of 300 to 500° C. in the presence of a fluorination catalyst to fluorinate the chlorine compounds. The present invention has been accomplished based on this finding.

Accordingly, the present invention comprises, for example, the following matters [1] to [19].

[1] A process for producing hexafluoroethane, comprising a step of distilling a crude hexafluoroethane containing chlorine compounds each having two carbon atoms to distill out hexafluoroethane as a top flow from the top of a distillation column and separate a hexafluoroethane mixture containing the chlorine compounds as a bottom flow from the bottom of the distillation column, and a step of contacting the bottom flow with hydrogen fluoride in a gas phase at a temperature of 300 to 500° C. in the presence of a fluorination catalyst to fluorinate the chlorine compounds.

[2] A process for producing hexafluoroethane, comprising (I) a step of producing a crude hexafluoroethane containing chlorine compounds each having two carbon atoms, (II) a step of distilling the crude hexafluoroethane to distill out hexafluoroethane as a top flow from the top of a distillation column and separate a hexafluoroethane mixture containing the chlorine compounds as a bottom flow from the bottom of the distillation column, and (III) a step of contacting the bottom flow with hydrogen fluoride in a gas phase at a temperature of 300 to 500° C. in the presence of a fluorination catalyst to fluorinate the chlorine compounds.

[3] The process for producing hexafluoroethane as described in [1] or [2] above, wherein the chlorine compound having two carbon atoms contained in the crude hexafluoroethane is at least one compound selected from the group consisting of dichlorotetrafluoroethane, chloropentafluoroethane, 1-chloro-2,2,2-trifluoroethane, 1,1-dichloro-2,2,2-trifluoroethane and 1-chloro-1,2,2,2-tetrafluoroethane.

[4] The process for producing hexafluoroethane as described in any one of [1] to [3] above, wherein the top flow contains at least 80 vol % of the hexafluoroethane introduced into the distillation column.

[5] The process for producing hexafluoroethane as described in any one of [1] to [4] above, wherein the fluorination catalyst is a supported or bulk catalyst comprising a trivalent chromium oxide as the main component.

[6] The process for producing hexafluoroethane as described in any one of [1] to [5] above, wherein the molar ratio of the hydrogen fluoride to the hexafluoroethane mixture contained in the bottom flow (hydrogen fluoride/hexafluoroethane mixture) is from 0.05 to 10.

[7] The process for producing hexafluoroethane as described in any one of [1] to [6] above, wherein the concentration of the chlorine compounds contained in the hexafluoroethane mixture is 1 vol % or less.

[8] The process for producing hexafluoroethane as described in any one of [1] to [7] above, wherein the crude hexafluoroethane is a gas obtained by reacting dichlorotetrafluoroethane and/or chloropentafluoroethane with hydrogen fluoride in the gas phase in the presence of a fluorination catalyst.

[9] The process for producing hexafluoroethane as described in any one of [1] to [7] above, wherein the crude hexafluoroethane is a gas obtained by reacting 1,1,1,2-tetrafluoroethane and/or pentafluoroethane, containing the chlorine compounds as impurities, with a fluorine gas.

[10] The process for producing hexafluoroethane as described in [9] above, wherein the reaction with the fluorine gas is carried out in a gas phase in the presence of a diluent gas.

[11] The process for producing hexafluoroethane as described in [10] above, wherein the diluent gas is a gas containing at least one of tetrafluoromethane, hexafluoroethane, octafluoropropane and hydrogen fluoride.

[12] The process for producing hexafluoroethane as described in [10] or [11] above, wherein the diluent gas is a gas rich in hydrogen fluoride.

[13] The process for producing hexafluoroethane as described in any one of [9] to [12] above, wherein the reaction with the fluorine gas is carried out at a temperature of 250 to 500° C.

[14] The process for producing hexafluoroethane as described in any one of [9] to [13] above, wherein the concentration of 1,1,1,2-tetrafluoroethane at the inlet of a reactor is 4 mol % or less in the reaction with the fluorine gas.

[15] The process for producing hexafluoroethane as described in any one of [9] to [13] above, wherein the concentration of pentafluoroethane at the inlet of a reactor is 6 mol % or less in the reaction with the fluorine gas.

[16] The process for producing hexafluoroethane as described in any one of [9] to [15] above, wherein the reaction with the fluorine gas is carried out under a pressure of 0 to 3 MPa.

[17] The process for producing hexafluoroethane as described in any one of [2] to [16] above, wherein after removing acidic components from the gas obtained through the step (III), at least a part of the gas is re-circulated to the step (I) and/or the step (II).

[18] A hexafluoroethane product comprising hexafluoroethane obtained by the production process described in any one of [1] to [17] above, in which the content of chlorine compounds each having two carbon atoms contained in the hexafluoroethane is 1 vol ppm or less.

[19] A cleaning gas comprising the hexafluoroethane product described in [18] above.

BEST MODE FOR CARRYING OUT THE INVENTION

Figure 1:
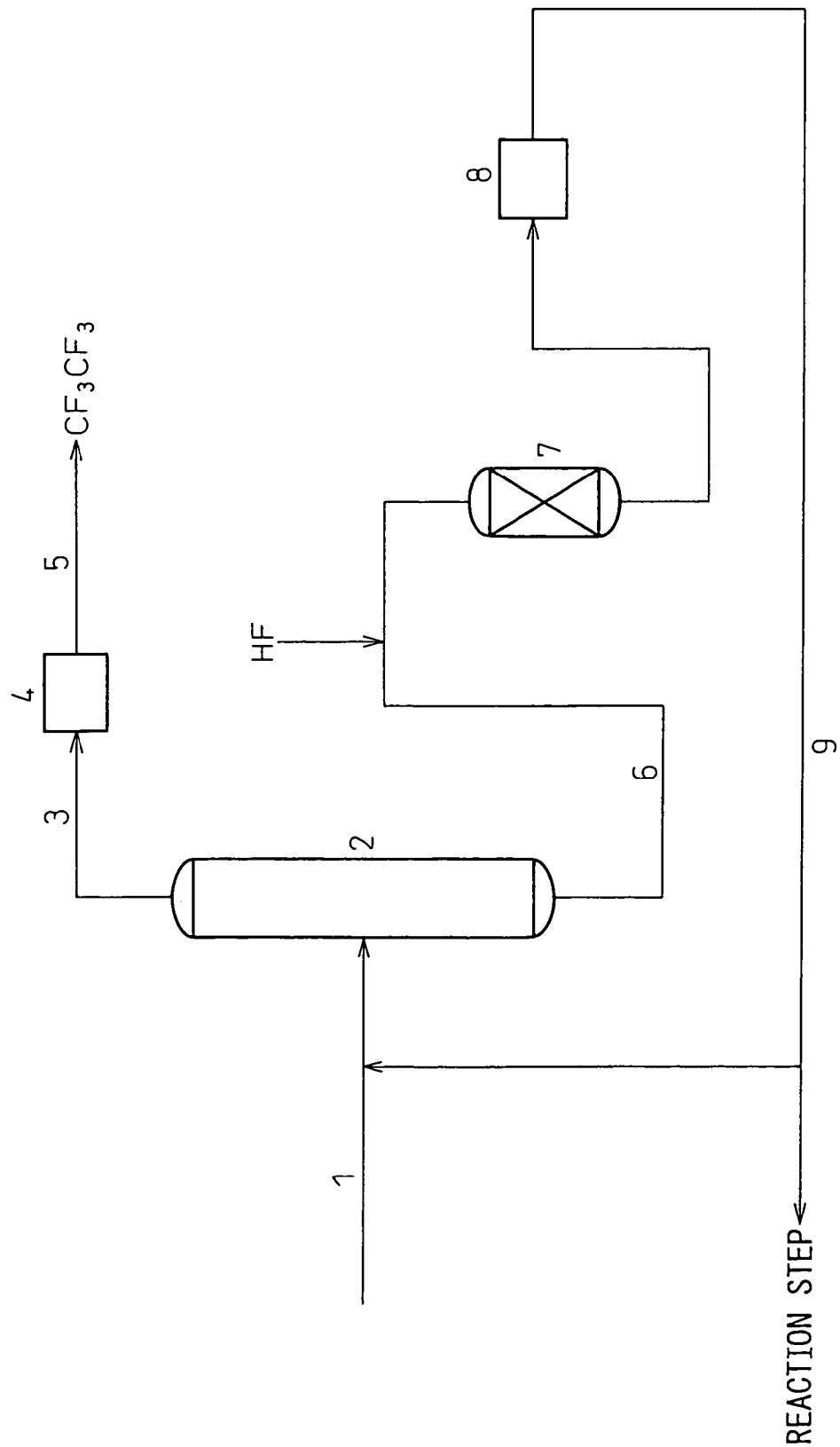
FIG. 1 is a schematic view of an apparatus which can be used in the process of the present invention.

Preferred embodiments of the production process for hexafluoroethane of the present invention and uses thereof are described in detail below.

Regarding the production process of hexafluoroethane, as described above, various methods have been heretofore known. Among these, the industrially safe and economical methods include:

(1) a method of fluorinating dichlorotetrafluoroethane, chloropentafluoroethane or the like by using hydrogen fluoride in the presence of a fluorination catalyst, and (2) a method of fluorinating tetrafluoroethane or pentafluoroethane by using a fluorine gas.

In the method (1) or (2), the compounds used as the starting material, such as dichlorotetrafluoroethane, chloropentafluoroethane and pentafluoroethane, can be produced starting from, for example, tetrachloroethylene ($CCl_2=CCl_2$). Also, the compounds such as 1,1,1,2-tetrafluoroethane can be produced starting from tricloroethylene ($CHCl=CCl_2$). Accordingly, whichever method is used, chlorine-containing compounds originated in raw materials are contained as impurities in the produced hexafluoroethane and the impurity content tends to increase as the reaction temperature is higher.

For example, in pentafluoroethane ($CF_3CHF_2$) which is commercially available as a refrigerant, chlorine-containing compounds such as chloromethane, chlorodifluoromethane, chloropentafluoroethane, dichlorotetrafluoroethane, chlorotetrafluoroethane and chlorotrifluoroethane are contained as impurities. In the case of producing $CF_3CF_3$ by a direct fluorination reaction of pentafluoroethane containing these chlorine-containing compounds with a fluorine gas, the chlorine-containing compounds contained in pentafluoroethane react with the fluorine gas to produce, for example, chlorine, hydrogen chloride, chlorine fluoride or different kinds of chlorofluorocarbons. Chloropentafluoroethane scarcely reacts with the fluorine gas but, for example, chlorotetrafluoroethane ($CF_3CHClF$) or chlorotrifluoroethane ($CF_3CH_2Cl$) reacts with the fluorine gas to produce chloropentafluoroethane. This chloropentafluoroethane and $CF_3CF_3$ do not form an azeotropic mixture but in the distillation system, these are concentrated (recovered) as a high boiling component in the bottom of the distillation tower. The main component in this bottom concentrate is $CF_3CF_3$ and its concentration is usually from about 90 to 97 mol %, but according to the concentration degree of impurities such as chlorine-containing compounds described above, the concentrate is discarded by burning or the like. However, this leads to the loss of $CF_3CF_3$ and, to avoid the loss, its recovery or treatment to a high purity by purification or the like is necessary.

The production process of hexafluoroethane of the present invention comprises a step of distilling a crude hexafluoroethane containing chlorine compounds each having two carbon atoms to distill out hexafluoroethane as a top flow from the top of a distillation column and separate a hexafluoroethane mixture containing the chlorine compounds as a bottom flow from the bottom of the distillation column, and a step of contacting the bottom flow with hydrogen fluoride in a gas phase at a temperature of 300 to 500° C. in the presence of a fluorination catalyst to fluorinate the chlorine compounds.

The top flow preferably contains at least 80 vol % of the hexafluoroethane introduced into the distillation column. If the hexafluoroethane distilled out from the top of the distillation column is less than 80 vol %, hexafluoroethane contained in the bottom flow may become a large amount so that the amount of the materials to be recycled becomes undesirably large.

As described above, the hexafluoroethane mixture contains 90 mol % or more of $CF_3CF_3$ and contains, as chlorine compounds each having two carbon atoms, at least one compound selected from dichlorotetrafluoroethane, chloropentafluoroethane, 1-chloro-2,2,2-trifluoroethane, 1,1-dichloro-2,2,2-trifluoroethane and 1-chloro-1,2,2,2-tetrafluoroethane.

The fluorination catalyst for use in the production process of hexafluoroethane of the present invention is preferably a supported or bulk catalyst comprising a trivalent chromium oxide as the main component. Also, a catalyst containing nickel, zinc, indium and/or gallium at an atomic ratio of 0.01 to 0.6 to chromium is preferably used. In the case where the catalyst is a supported catalyst, the support is preferably, for example, activated carbon, alumina or partially fluorinated alumina and the percentage of the component supported is preferably 30 mass % or less. The fluorination catalyst is preferably fluorinated with hydrogen fluoride or the like before use in the reaction.

At the time of contacting a hexafluoroethane mixture containing chlorine-containing compounds each having two carbon atoms with hydrogen fluoride in the presence of the above-described fluorination catalyst, the temperature is suitably from 300 to 500° C., preferably 350 to 450° C. If the temperature is less than 300° C., the chlorine-containing compound may be less fluorinated, whereas if the temperature exceeds 500° C., this may disadvantageously tend to cause shortening of the catalyst life and an increase of impurities.

In the reaction of fluorinating chlorine-containing compounds contained in the hexafluoroethane mixed gas, the molar ratio of the hydrogen fluoride to the hexafluoro-ethane mixed gas (hydrogen fluoride/hexafluoroethane mixed gas) is preferably from 0.05 to 10, more preferably from 0.1 to 5. If the molar ratio of the hydrogen fluoride to the hexafluoroethane mixed gas is less than 0.05, this may tend to cause production of different kinds of chlorofluorocarbons due to side reaction or the like or deterioration of the catalyst due to caulking or the like, whereas if it exceeds 10, a large reactor may be necessary or problems such as recovery of unreacted hydrogen fluoride may arise and this may not be profitable.

The concentration of chlorine-containing compounds contained in the hexafluoroethane mixed gas is preferably 1 vol % or less. If the concentration of chlorine-containing compounds exceeds 1 vol %, it may be necessary to, for example, more elevate the reaction temperature or enlarge the reactor, and the profitability may sometimes decrease.

The crude hexafluoroethane is preferably a gas obtained by reacting dichlorotetrafluoroethane and/or chloropentafluoroethane with hydrogen fluoride in the gas phase in the presence of a fluorination catalyst. The crude hexafluoroethane is more preferably a gas obtained by reacting 1,1,1,2-tetrafluoroethane and/or pentafluoroethane with a fluorine gas.

Preferably, the reaction for producing the crude hexafluoroethane is carried out by reacting 1,1,1,2-tetrafluoroethane and/or pentafluoroethane with a fluorine gas in a gas phase in the presence of a diluting gas.

The method of direct fluorination using a fluorine gas may cause a risk of an explosive reaction of the substrate organic compounds with the fluorine gas, corrosion of the equipment or the like due to the use of the extremely highly reactive fluorine gas, and further cause a risk of the breakage of C—C bonds or occurrence of polymerization due to the heat generation, the occurrence of rapid reaction due to the generation or accumulation of carbon, etc., or the occurrence of side reaction such as explosion.

The reaction heat is proportioned to the mole number of fluorine and becomes larger as the amount of fluorine becomes larger. Thus, the breakage of C—C bonds due to the heat generation, explosion and the like may easily occur, and in addition, the yield of the products may be decreased, thereby causing problems in industrial production or practical operation. Therefore, it is preferable that the fluorine gas is diluted with an inert gas such as nitrogen or helium for inhibiting the rapid generation of the reaction heat in the direct fluorination method.

The diluting gases may generally include inert gases such as nitrogen, helium and argon, but the use of these gases may not be advantageous from the view point of cost when taking the separation of hexafluoroethane from these inert gases for purification of hexafluoroethane into consideration. Therefore, the use of a component containing at least one of tetrafluoromethane (having a boiling point of −127.9° C.), hexafluoroethane (having a boiling point of −78.5° C.), octafluoropropane (having a boiling point of −37.7° C.) and hydrogen fluoride (having a boiling point of 20° C.) as the diluting gas can provide the advantage of suppressing the burning or explosion and, in addition, the advantage in energy cost for separation and purification since these gases have a higher boiling points as compared with helium (having a boiling point of −268.9° C.) and the like. Hexafluoroethane is just the reaction product of the subject process and, therefore, the purification step can be carried out as it stands. More preferably, a component rich in hydrogen fluoride can also be used as the diluting gas.

For example, 1 mole of hexafluoroethane and 2 moles of hydrogen fluoride are produced from the reaction of 1 mole of 1,1,1,2-tetrafluoroethane with 2 moles of fluorine. The difference in boiling point between the subject hexafluoroethane and the by-produced hydrogen fluoride is about 100° C. and the component rich in hydrogen fluoride can be obtained by a simple method such as partial condensation, and therefore, the use of this component is economical. Hydrogen fluoride may also be newly added as a diluting gas. Further, as mentioned above, the generation or accumulation of carbon due to the breakage of C—C bonds, etc. during the reaction for long period of time occurs in the direct fluorination method using a fluorine gas and the generation or accumulation of carbon may cause a risk of the occurrence of rapid reaction with the fluorine gas or explosion. However, by the use of hydrogen fluoride as the diluting gas, the generation or accumulation of carbon can be suppressed. Here, the component rich in hydrogen fluoride refers to a component containing hydrogen fluoride as the main component.

The reaction may be carried out in the presence of the reaction substrate, the fluorine gas and the diluting gas, but in general, the either one or both of the reactive substrate and the fluorine gas may be diluted with the diluting gas before being introduced into the reactor and then introduced into the reactor. In view of the safety, it is preferable that the reaction substrate and the fluorine gas are both diluted with the diluting gas in a concentration as low as possible.

When the reaction with the fluorine gas is carried out, it is preferable that the concentration of 1,1,1,2-tetrafluoroethane at the inlet of a reactor is 4 mol % or less and the concentration of pentafluoroethane at the inlet of a reactor is 6 mol % or less. These materials can be used alone or in combination. Taking the above-mentioned facts, that an extremely high reaction heat is generated with the reaction of the organic compounds with a fluorine gas and the reaction heat is proportioned to the mole number of fluorine and becomes larger as the amount of fluorine becomes larger, into consideration, the control of the reaction heat in question becomes easier as the amount of substitution of H with F is smaller so that the amount of the expensive florine used can be reduced.

The reaction temperature may preferably be 250 to 500° C. and the reaction pressure may preferably be 0 to 3 MPa. The pressure refers to a gauge pressure.

When the reaction is carried out by using one or more hydrofluorocarbons and a fluorine gas in the presence of the above-mentioned diluting gas, the reaction temperature may also be one of the important conditions in order to cause the fluorination reaction to be effectively proceeded. The optimum range of the reaction temperature may very depending on the contact time and the kind of the hydrofluorocarbons used as the starting materials. For example, in the case of the reaction of 1,1,1,2-tetrafluoroethane with fluorine, when the contact time is large (contact time of 15 seconds), the reaction is initiated at the temperature of about 50° C. and the conversion becomes about 100% at a temperature of about 250° C. The reaction temperature may be a raised one and preferably in a range of 250 to 500° C.

If the reaction temperature is lower than 250° C., the conversion of the hydrofluorocarbons may be reduced, whereas if the reaction temperature is higher than 500° C., the breakage of C—C bonds, polymerization and the like may occur to lower the yield of the product and also the corrosion of the reactor, etc. and an increase of the energy cost may undesirably be caused.

The contact time is not particularly be limited, but in general, may be preferably 1 to 30 seconds, more preferably 3 to 30 seconds since a larger reactor should be used as the contact time is increased in a range of 0.1 to 120 seconds, for example, which is uneconomical. Further, it may also be important to blend the reaction substrate and the fluorine gas well. As the extremely highly reactive fluorine gas is used in the direct fluorination method as mentioned above, there may be a risk in that the substrate organic compounds (particularly hydrogen-containing compounds) may be caused to be burnt or explode when they are contacted with fluorine.

In the direct fluorination reaction, as hydrofluorocarbons containing hydrogen are used as the substarate organic compounds, it is an important point to prevent the explosion of the hydrofluorocarbons and fluorine. In order to prevent the explosion, it is necessary to keep the composition of the mixed gas outside the explosion range. The present inventors have measured the explosion range of the hydrofluorocarbon/fluorine mixture, and found that lower limit of the concentration of pentafluoroethane is about 6% and that of the concentration of 1,1,1,2-tetrafluoroethane is about 4%. The safety ranges of the concentrations of the organic compounds at the reactor inlet have been defined based on this finding.

The molar ratio of the fluorine gas to the hydrofluorocarbons to be fed into the reaction system may be in a range of preferably 0.5 to 5.0, more preferably 1.0 to 3.0. If the mole ratio of the fluorine gas fed is lower than 0.5, the reaction may not proceed as desirably to deteriorate the efficiency of the process, whereas if the ratio is higher than 5.0, the fluorine gas is excessive so that equipments for the collection thereof become necessary to make the process uneconomical. When the reaction with fluorine is carried out, the reaction pressure may also be important in order to suppress the risk of explosion and the like. As the risk of explosion is increased as the pressure becomes higher, the reaction may desirably be carried out under a low pressure, preferably in a range of 0 to 3 MPa. The material of the reactor may referably be one resistant to corrosion by corrosive gases and may include, for example, nickel, inconel and hastelloy.

For example, as shown in the following formulae (1) to (3), the chlorine compound having two carbon atoms reacts with hydrogen fluoride in the presence of a fluorination catalyst to produce hexafluoroethane or a hydrofluorocarbon.

$$CCl_2FCF_3 + 2HF \rightarrow CF_3CF_3 + 2HCl \qquad (1)$$

$$CClF_2CF_3 + HF \rightarrow CF_3CF_3 + HCl \qquad (2)$$

$$CHClFCF_3 + HF \rightarrow CHF_2CF_3 + HCl \qquad (3)$$

In this way, the impurity chlorine-containing compound reacts with hydrogen fluoride to produce $CF_3CF_3$ or hydrofluorocarbon. The product is a mixed gas mainly comprising $CF_3CF_3$, hydrofluorocarbon, hydrogen chloride and hydrogen fluoride, and acid contents such as hydrogen chloride and hydrogen fluoride are preferably removed. As for the method of removing the acid contents, for example, a method of contacting the gas with a purifying agent or a method of contacting the gas with water, an aqueous alkali solution or the like can be used. After the removal of acid contents, the gas containing $CF_3CF_3$ or hydrofluorocarbon is preferably dehydrated by using a dehydrating agent such as zeolite. At least a part of the gas after removal of acid components is preferably re-circulated to the step of producing a crude hexafluoroethane and/or the step of distilling and purifying the crude hexafluoroethane.

By using the production process of the present invention, hexafluoroethane having a purity of 99.9997 vol % or more can be obtained. In this case, the content of chlorine compounds each having two or more carbon atoms contained as impurities is 1 vol ppm or less. The purity of hexafluoroethane and the content of impurities can be analyzed by gas chromatography (GC) or by using a device such as gas chromatography mass spectrometer (GC-MS).

Uses of high-purity hexafluoroethane obtained by using the production process of the present invention are described below.

The high-purity hexafluoroethane or a mixed gas thereof with an inert gas such as He, Ar and $N_2$ or with a gas such as $O_2$ and $NF_3$ (in the present invention, these are collectively called a "hexafluoroethane product") can be used as an etching gas at the etching step in the process of producing a semiconductor device and also can be used as a cleaning gas at the cleaning step in the process of producing a semiconductor device. In the process of producing a semiconductor device such as LSI and TFT, a thin or thick film is formed by using CVD, sputtering or vapor deposition, and then etched to form a circuit pattern. In the apparatus for forming a thin or thick film, cleaning is performed for removing unnecessary deposits accumulated on the inner wall of apparatus, jigs and the like, because the produced unnecessary deposits cause generation of particles and must be removed occasionally so as to produce a film having good quality.

The etching using hexafluoroethane can be performed under various dry etching conditions such as plasma etching and microwave etching, and the hexafluoroethane may be used by mixing it with an inert gas such as He, $N_2$ and Ar or with a gas such as HCl, $O_2$, $H_2$, $F_2$ and $NF_3$, at an appropriate ratio.

The present invention is described in greater detail below by referring to Examples, but the present invention is not limited to these Examples.

REFERENTIAL EXAMPLE

Production of Pentafluoroethane

Tetrachloroethylene ($CCl_2$=$CCl_2$) was reacted with hydrogen fluoride (HF) in the presence of a chromium-based fluorination catalyst (first reaction) (reaction pressure: 0.4 MPa, reaction temperature: 320° C., HF/tetrachloroethylene=8 (by mol)). Then, mainly dichlorotrifluoroethane ($CF_3CHCl_2$) and chlorotetrafluoroethane ($CF_3CHClF$) obtained in the first reaction were reacted with hydrogen fluoride (second reaction) (reaction pressure: 0.45 MPa, reaction temperature: 330° C., HF/($CF_3CHCl_2$+$CF_3CHClF$)=6 (by mol)). After the completion of second reaction, removal of acid contents, distillation and purification were performed by a known method to obtain a distillate containing pentafluoroethane as the main component. This distillate was analyzed by gas chromatography and found to be pentafluoroethane having the composition shown in Table 1 below.

TABLE 1

| Name of Compound | Concentration (vol %) |
| --- | --- |
| $CF_3CHF_2$ | 99.9508 |
| $CHF_3$ | 0.0006 |
| $CH_2F_2$ | 0.0024 |
| $CF_3CHCl_2$ | 0.0009 |
| $CF_3CHClF$ | 0.0006 |
| $CF_3CClF_2$ | 0.0246 |
| $CF_3CH_3$ | 0.0194 |
| Others | 0.0007 |

Example 1

Production of Crude Hexafluoroethane

Into an Inconel 600-type reactor (using a heating system by an electric heater; the reactor had been subjected to a passivation treatment with fluorine gas at a temperature of 500° C.) having an inner diameter of 20.6 mm and a length of 500 mm, a nitrogen gas was passed from two gas inlets at a total flow rate of 30 NL/h. The temperature in the reactor was kept at 380° C. Then, hydrogen fluoride was passed from those two gas inlets at a total flow rate of 50 NL/h and the pentafluoroethane obtained in Referential Example was introduced from one gas inlet at a flow rate of 3.6 NL/h. Also, a fluorine gas was introduced from another gas inlet at a flow rate of 3.9 NL/h, whereby a direct fluorination reaction was performed. The gas distilled out from the reactor was contacted with an aqueous potassium hydroxide solution and an aqueous potassium iodide solution to remove acid contents such as hydrogen fluoride and unreacted fluorine gas contained in the gas distilled out, and then dried by contacting it with a dehydrating agent. The gas after drying was collected under cooling and the collected gas was introduced into a distillation column. A low boiling content was distilled out from the top and a crude hexafluoroethane was obtained as the bottom distillate of a first distillation column shown in FIG. 1 from the bottom. The composition of the crude hexafluoroethane obtained is shown in Table 2.

TABLE 2

| Name of Compound | Concentration (vol %) |
| --- | --- |
| $CF_3CF_3$ | 99.8326 |
| $CF_3CH_2F$ | 0.0007 |
| $CH_3CHF_2$ | 0.1225 |
| $CF_3CCl_2F$ | 0.0009 |
| $CF_3CClF_2$ | 0.0258 |
| $C_4F_{10}$ | 0.0162 |
| Others | 0.0013 |

Example 2

Distillation of Crude Hexafluoroethane

In FIG. 1, the crude hexafluoroethane corresponding to the first distillation column bottom distillate 1 was introduced into a second distillation column 2 and continuously distilled, and mainly hexafluoroethane was recovered as the top distillate 3 and passed through an adsorptive purification device 4 to obtain high-purity hexafluoroethane 5. The composition thereof is shown in Table 3. Also, a hexafluoroethane mixture was obtained as the second distillation column bottom distillate 6. The composition thereof is shown in Table 4.

TABLE 3

| Name of Compound | Concentration (vol %) |
| --- | --- |
| $CF_3CF_3$ | 99.9998 |
| $CF_3CHF_2$ | <0.0001 |
| $CF_3CClF_2$ | <0.0001 |

TABLE 4

| Name of Compound | Concentration (vol %) |
| --- | --- |
| $CF_3CF_3$ | 95.2236 |
| $CF_3CH_2F$ | 0.0193 |
| $CF_3CHF_2$ | 3.3726 |
| $CF_3CCl_2F$ | 0.0248 |
| $CF_3CClF_2$ | 0.7104 |
| $C_4F_{10}$ | 0.4461 |
| Others | 0.0358 |

Example 3

Preparation of Catalyst

In a 10 L-volume vessel, 0.6 L of pure water was poured and stirred. Thereto, a solution obtained by dissolving 452 g of $Cr(NO_3)_3 \cdot 9H_2O$ and 42 g of $In(NO_3)_3 \cdot nH_2O$ (n=about 5) in 1.2 L of pure water, and 0.31 L of a 28% aqueous ammonia were added dropwise over about 1 hour while controlling the flow rates of two aqueous solutions to keep the reaction solution at a pH of 7.5 to 8.5. The obtained slurry was separated by filtration and the solid resulting from separation by filtration was thoroughly washed with pure water and then dried at 120° C. for 12 hours. The dried solid was ground and then mixed with graphite and the mixture was formed into pellets by a tablet-shaping machine. The pellets were fired at 400° C. for 4 hours in a nitrogen stream to obtain a catalyst precursor. The catalyst precursor obtained was filled in an Inconel-made reactor and subjected first to a fluorination treatment (activation of catalyst) at 350° C. under atmospheric pressure in a hydrogen fluoride stream diluted with nitrogen and then to a fluorination treatment (activation of catalyst) at 450° C. in a 100% hydrogen fluoride stream and further in a hydrogen fluoride stream diluted with nitrogen to prepare a catalyst.

Example 4

Fluorination Reaction of Hexafluoroethane Mixture 6

As shown in FIG. 1, in an Inconel 600-type reactor 7 having an inner diameter of 1 inch and a length of 1 m, 120 ml of the catalyst obtained in Example 3 was filled and kept at a temperature of 450° C. while passing nitrogen. Thereto, hydrogen fluoride was fed at 2.8 NL/hr and then the second distillation column bottom distillate 6 comprising a hexafluoroethane mixture, obtained in Example 2, was fed at 2.8 NL/h. Thereafter, the feeding of nitrogen gas was stopped and the reaction was started. After about 4 hours, the outlet gas from the reactor was passed through an acid content-removing device 8 and the resulting purified gas 9 was analyzed by gas chromatography, as a result, a gas having a composition shown in Table 5 was obtained.

TABLE 5

| Name of Compound | Concentration (vol %) |
|---|---|
| $CF_3CF_3$ | 96.0876 |
| $CF_3CH_2F$ | 0.0189 |
| $CF_3CHF_2$ | 3.3688 |
| $CF_3CCl_2F$ | 0.0002 |
| $CF_3CClF_2$ | 0.0365 |
| $C_4F_{10}$ | 0.4482 |
| Others | 0.0398 |

As apparent from these results, about 95% of chlorine compounds each having two carbon atoms contained in the crude hexafluoroethane were converted into hexafluoroethane by the fluorination reaction and this reveals that the chlorine-containing compound could be prevented from concentrating and the unit productivity was elevated.

Also, the gas after purification was re-circulated to the distillation system, but the composition of high-purity hexafluoroethane 5 was not changed from the composition shown in Example 2 and the concentration of the chlorine compounds each having two carbon atoms was 1 vol ppm or less. Furthermore, the purified gas was re-circulated to the reaction step (direct fluorination step by a fluorine gas), as a result, about 99% of pentafluoroethane contained in the purified gas was converted into hexafluoroethane by the reaction with fluorine gas.

INDUSTRIAL APPLICABILITY

According to the present invention, an industrially advantageous process for producing hexafluoroethane which can be used mainly as a cleaning gas in the production process of a semiconductor device, and uses of the hexafluoroethane, can be provided.

The invention claimed is:

1. A process for producing hexafluoroethane, comprising a step of distilling a crude hexafluoroethane containing chlorine compounds each having two carbon atoms to distill out hexafluoroethane as a top flow from the top of a distillation column and separate a hexafluoroethane mixture containing said chlorine compounds as a bottom flow from the bottom of the distillation column, and a step of contacting said bottom flow with hydrogen fluoride in the gas phase at a temperature of 300 to 500° C. in the presence of a fluorination catalyst to fluorinate said chlorine compounds.

2. A process for producing hexafluoroethane, comprising (I) a step of producing a crude hexafluoroethane containing chlorine compounds each having two carbon atoms, (II) a step of distilling said crude hexafluoroethane to distill out hexafluoroethane as a top flow from the top of a distillation column and separate a hexafluoroethane mixture containing said chlorine compounds as a bottom flow from the bottom of the distillation column, and (III) a step of contacting said bottom flow with hydrogen fluoride in the gas phase at a temperature of 300 to 500° C. in the presence of a fluorination catalyst to fluorinate said chlorine compounds.

3. The process for producing hexafluoroethane as claimed in claim 1, wherein the chlorine compound having two carbon atoms contained in said crude hexafluoroethane is at least one compound selected from the group consisting of dichlorotetrafluoroethane, chloropentafluoroethane, 1-chloro-2,2,2-trifluoroethane, 1,1-dichloro-2,2,2-trifluoroethane and 1-chloro-1,2,2,2-tetrafluoroethane.

4. The process for producing hexafluoroethane as claimed in claim 1, wherein the top flow contains at least 80 vol % of the hexafluoroethane introduced into the distillation column.

5. The process for producing hexafluoroethane as claimed in claim 1, wherein said fluorination catalyst is a supported or bulk catalyst comprising a trivalent chromium oxide as the main component.

6. The process for producing hexafluoroethane as claimed in claim 1, wherein the molar ratio of the hydrogen fluoride to the hexafluoroethane mixture contained in said bottom flow (hydrogen fluoride/hexafluoroethane mixture) is from 0.05 to 10.

7. The process for producing hexafluoroethane as claimed in claim 1, wherein the concentration of said chlorine compounds contained in said hexafluoroethane mixture is 1 vol % or less.

8. The process for producing hexafluoroethane as claimed in claim 1, wherein said crude hexafluoroethane is a gas obtained by reacting dichlorotetrafluoroethane and/or chloropentafluoroethane with hydrogen fluoride in the gas phase in the presence of a fluorination catalyst.

9. The process for producing hexafluoroethane as claimed in claim 1, wherein said crude hexafluoroethane is a gas obtained by reacting 1,1,1,2-tetrafluoroethane and/or pentafluoroethane, containing the chlorine compounds as impurities, with a fluorine gas.

10. The process for producing hexafluoroethane as claimed in claim 9, wherein the reaction with the fluorine gas is carried out in a gas phase in the presence of a diluent gas.

11. The process for producing hexafluoroethane as claimed in claim 10, wherein the diluent gas is a gas containing at least one of tetrafluoromethane, hexafluoroethane, octafluoropropane and hydrogen fluoride.

12. The process for producing hexafluoroethane as claimed in claim 10, wherein the diluent gas is a gas rich in hydrogen fluoride.

13. The process for producing hexafluoroethane as claimed in claim 9, wherein the reaction with the fluorine gas is carried out at a temperature of 250 to 500° C.

14. The process for producing hexafluoroethane as claimed in claim 9, wherein the concentration of 1,1,1,2-tetrafluoroethane at the inlet of a reactor is 4 mol % or less in the reaction with the fluorine gas.

15. The process for producing hexafluoroethane as claimed in claim 9, wherein the concentration of pentafluoroethane at the inlet of a reactor is 6 mol % or less in the reaction with the fluorine gas.

16. The process for producing hexafluoroethane as claimed in claim 9, wherein the reaction with the fluorine gas is carried out under a pressure of 0 to 3 MPa.

17. The process for producing hexafluoroethane as claimed in claim 2, wherein after removing acidic components from the gas obtained through said step (III), at least a part of said gas is re-circulated to the step (I) and/or the step (II).

18. The process for producing hexafluoroethane as claimed in claim 1, wherein the hexafluoroethane mixture contains 90 mol % or more of $CF_3CF_3$.

19. The process for producing hexafluoroethane as claimed in claim 2, wherein the hexafluoroethane mixture contains 90 mol % or more of $CF_3CF_3$.

\* \* \* \* \*